United States Patent [19]

Takahashi et al.

[11] 4,437,880
[45] Mar. 20, 1984

[54] N'-PHENYL-N-METHYLUREA DERIVATIVES

[75] Inventors: Junya Takahashi, Nishinomiya; Ichiki Takemoto, Takarazuka; Katsuzo Kamoshita, Osaka; Ryo Yoshida, Kawanishi; Haruhiko Katoh; Seizo Sumida, both of Nishinomiya, all of Japan

[73] Assignee: Sumitomo Chemical Company, Limited, Osaka, Japan

[21] Appl. No.: 269,851

[22] Filed: May 28, 1981

[30] Foreign Application Priority Data

May 28, 1980 [JP] Japan .................. 55-71938

[51] Int. Cl.³ .................. A01N 47/30; C07C 127/19
[52] U.S. Cl. .................. 71/120; 260/453 RW; 260/453 AR; 260/500.5 H; 564/48; 564/305; 568/928
[58] Field of Search .................. 260/453 RW; 564/48; 71/120

[56] References Cited

U.S. PATENT DOCUMENTS

| | | | |
|---|---|---|---|
| 4,123,256 | 10/1978 | Yoshida et al. | 71/105 |
| 4,129,436 | 12/1978 | Takemoto et al. | 71/120 |
| 4,144,049 | 3/1979 | Yoshida et al. | 71/120 |
| 4,249,938 | 2/1981 | Takemoto et al. | 71/98 |

FOREIGN PATENT DOCUMENTS 2010244 6/1979 United Kingdom .

*Primary Examiner*—Dolph H. Torrence
*Attorney, Agent, or Firm*—Birch, Stewart, Kolasch & Birch

[57] ABSTRACT

A compound of the formula:

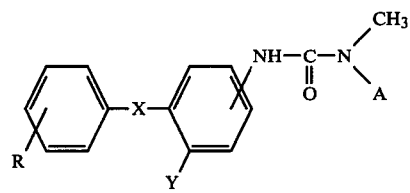

wherein R is a hydrogen atom or a $C_1$–$C_4$ alkyl group, X is a $C_3$–$C_4$ alkylene group or a $C_3$ alkenylene group, Y is a hydrogen atom or a chlorine atom, A is a methyl group or a methoxy group and the substituted ureido group is present at the m- or p-position to the group of the formula:

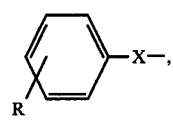

which is useful as a herbicide.

8 Claims, No Drawings

N'-PHENYL-N-METHYLUREA DERIVATIVES

The present invention relates to N'-phenyl-N-methylurea derivatives, and their production and use.

The said N'-phenyl-N-methylurea derivatives (hereinafter referred to as "methylurea derivative(s)") are representable by the formula:

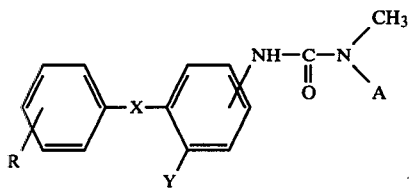

wherein R is a hydrogen atom or a $C_1$-$C_4$ alkyl group (e.g. methyl, ethyl, propyl, butyl), X is a $C_3$-$C_4$ alkylene group (e.g. trimethylene, tetramethylene) or a $C_3$ alkenylene group (propenylene), Y is a hydrogen atom or a chlorine atom, A is a methyl group or a methoxy group and the substituted ureido group is present at the m- or p-position to the group of the formula:

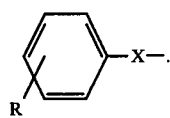

Among them, particularly preferred are those of the formula (I) wherein X is a $C_3$-$C_4$ alkylene group, Y is a hydrogen atom and the substituted ureido group is present at the m-position to the group of the formula:

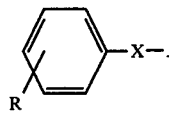

Rice (*Oryza sativa*), wheat (*Triticum aestivum*), corn (*Zea mays*), soybean (*Glycine max*), cotton (Gossypium spp.) and the like are crop plants of world-wide importance. In cultivation of these crop plants, chemical control of weeds is indispensable to prevent reductions in the yield. Particularly, it is a recent demand that the herbicides to be applied to these crop plants should have a selectivity such as a high potency against the weeds while exerting no or lesser damage to the crop plants.

Among urea derivatives, as is well known, there are compounds having a strong herbicidal activity such as N'-4-chlorophenyl-N,N-dimethylurea (monuron) and N'-3,4-dichlorophenyl-N,N-dimethylurea (diuron). It is also well known that the herbicidal activity of these urea derivatives is due to the inhibition of photosynthesis. Photosynthesis is a physiological function peculiar to plants and is not operative in mammals. Accordingly, it is highly predictable that specific inhibitors of photosynthetic processes do not afford any significant damage to mammals but can exterminate plants. In fact, herbicidal photosynthesis inhibitors such as monuron, diuron and 5-bromo-3-sec-butyluracil (bromacil) are all low in mammalian toxicity. However, they exert a herbicidal activity against higher plants because photosynthesis is common to higher plants. Due to this fact, most photosynthesis inhibitors are non-selective and do damage to crop plants. In order for a compound to be a selective herbicide, it should have both a strong herbicidal activity against weeds and a high selectivity to an intended crop plant. But, such a selective herbicide is very difficult to find out and can not easily be thought out systematically by mere analogy and modification of known chemical structures. Therefore, a highly detailed study with trial and error is necessary to find out such selective herbicides. For example, N'-3,4-dichlorophenyl-N-methoxy-N-methylurea (linuron) has a selectivity to Umbelliferae plants, but the compound havig a methyl group or an ethyl group in place of the methoxy group lacks the selectivity to said plants [Herbicide Handbook of The Weed Science Society of America, 3rd Ed., 172-176 and 221-225 (1974)]. Accordingly, the selective herbicidal activity requires a very specific chemical structure, and only a slight difference in the chemical structure brings about quite a large difference in degree and kind of selectivity.

Studies have been concentrated on phenylurea derivatives from the standpoint of low mammalian toxicity and strong herbicidal activity, and a diversified investigation has been carried out on how to impart selectivity to those derivatives. As the result, it has now been found that the methylurea derivatives (I) exhibit a strong herbicidal activity against a wide variety of weeds while preserving a high selectivity to various crop plants such as wheat when applied by a foliar treatment after germination of weeds.

Referring to the herbicidal activity of the methylurea derivatives (I) of the invention in more detail, they can exhibit a significant herbicidal activity in any of the treatment modes such as pre-emergence soil treatment, post-emergence foliar treatment and paddy field treatment, but their herbicidal activity is particularly notable in the post-emergence foliar treatment. In this mode, the methylurea derivatives (I) show a high selectivity to crop plants such as wheat, corn, soybean and cotton, among which the selectivity to wheat is especially remarkable as can be seen in the examples hereinafter presented. Namely, the application of the methylurea derivatives (I) to the field of wheat by foliar treatment can exterminate a wide variety of weeds including common lambsquarters (*Chenopodium album*), wild mustard (*Sinapis arvensis*), wild buckwheat (*Polygonum convolvalus*), common chickweed (*Stellaria media*), red deadnettle (*Lamium purpureum*), violet (*Viola arvensis*), quack grass (*Agropyron repens*), barnyard grass (*Echinochloa crus-galli*) and green foxtail (*Setaria viridis*) with no material toxicity to wheat. In regard to the herbicide to be applied in the field of wheat, there is a compound known as "isoproturon" (e.g. 3-(4-isopropylphenyl)-1,1-dimethylurea; hereinafter referred to as "Control (c)"). However, the herbicidal activity of this compound on broad-leaved weeds such as wild mustard, wild buckwheat, red deadnettle and violet is poor, as can be seen in the examples hereinafter presented. Accordingly, this compound is required to use together with any other herbicide effective in exterminating broad-leaved seeds. On the contrary, the methylurea derivatives (I) have themselves a strong herbicidal activity on broad-leaved weeds, without requiring any other herbicides, owing to their broad herbicidal spectra.

While the methylurea derivatives (I) of the invention are per se novel, there are some known compounds structurally related thereto. For instance, Belgian Pat.

No. 871,562 and U.S. Pat. No. 4,249,938 disclose respectively N'-3-(phenethyloxy)phenyl-N-methoxy-N-methylurea (hereinafter referred to as "Control (a)") and N'-4-[3-(4-methylphenyl)propoxy]phenyl-N,N-dimethylurea (hereinafter referred to as "Control (b)"). However, the methylurea derivatives (I) are much stronger than Controls (a) and (b) in herbicidal activity. In addition, the selectivity of the methylurea derivatives (I) is more excellent than those of Controls (a) and (b). Namely, comparison between N'-3-(3-phenylpropyl)-phenyl-N-methoxy-N-methylurea (Compound No. 4) and Control (a) and that between N'-4-[4-(4-methylphenyl)butyl]phenyl-N,N-dimethylurea (Compound No. 17) and Control (b) show: first, the invention compounds can exterminate broad-leaved weeds as well as Gramineae weeds in lesser dosage than the control compounds, particularly preserving a superior herbicidal activity against weeds in the wheat field to that of the control compounds; secondly, the invention compounds is less toxic to wheat than the control compounds. These advantageous properties of the methylurea derivatives (I) are attributable to their inherent chemical structure. In other words, replacement of the oxygen atom bonding the phenylalkyl group and the ureidophenyl group in Controls (a) and (b) by a methylene group results in enhancement of safety to wheat with improvement of a herbicidal activity against weeds. These enhancement and improvement are entirely of unexpected nature.

As described above, the methylurea derivatives (I) fallen within the invention commonly show a high selectivity to wheat. Among them, N'-4-(3-phenylpropyl)phenyl-N-methoxy-N-methylurea, N'-4-(3-phenylpropyl)phenyl-N,N-dimethylurea, N'-3-(3-phenylpropyl)phenyl-N-methoxy-N-methylurea, N'-3-(3-phenylpropyl)phenyl-N,N-dimethylurea, N'-3-[3-(3-methylphenyl)propyl]phenyl-N-methoxy-N-methylurea, N'-3-[3-(3-methylphenyl)propyl]phenyl-N,N-dimethylurea, N'-3-(4-phenylbutyl)phenyl-N,N-dimethylurea, N'-3-[3-(4-t-butylphenyl)propyl]phenyl-N-methoxy-N-methylurea, etc. exhibit in particular a strong herbicidal activity against weeds with a high selectivity to wheat.

Still, the methylurea derivatives (I) include some other compounds which can be safely used as herbicides in the field of corn, soybean or cotton by foliar treatment after germination of weeds such as redroot pigweed (*Amaranthus retroflexus*), common lambsquarters (*Chenopodium album*), coclkebur (*Xanthium pennsylvanicum*), Jimson weed (*Datura stramonium*), black nightshade (*Solanum nigrum*), sunflower (*Helianthus annuas*), annual morningglory (*Ipomoea purpurea*), velvetleaf (*Abutilon theopharasti*) and green foxtail (*Setaria viridis*), etc. Compounds having a selectivity to corn include, for example, N'-4-(3-phenylpropyl)phenyl-N,N-dimethylurea, N'-3-(3-phenylpropyl)phenyl-N,N-dimethylurea, N'-3-[3-(4-methylphenyl)propyl]phenyl-N-methoxy-N-methylurea, etc.; those having a selectivity to soybean include, for example, N'-4-[3-(4-methylphenyl)propyl]phenyl-N-methoxy-N-methylurea, N'-4-[3-(4-methylphenyl)propyl]phenyl-N,N-dimethylurea, N'-3-[3-(3-methylphenyl)propyl]phenyl-N-methoxy-N-methylurea, N'-3-[3-(3-methylphenyl)propyl]phenyl-N-methoxy-N-methylurea, etc.; and those having a selectivity to cotton include, for example, N'-4-(3-phenylpropyl)phenyl-N,N-dimethylurea, N'-3-(3-phenylpropyl)phenyl-N-methoxy-N-methylurea, N'-4-[3-(4-methylphenyl)propyl]phenyl-N,N-dimethylurea, N'-3-[3-(4-t-butylphenyl)propyl]phenyl-N-methoxy-N-methylurea, etc.

The methylurea derivatives (I) of the invention also show a strong herbicidal activity in the paddy field by a pre-emergence application or by an application at the initial stage of growth (within 10 days after transplantation) of paddy rice plants to control Gramineae weeds as well. Such Gramineae weeds include toothcup (*Rotala ramosion*), American waterwort (*Elatine americana*), false pimpernel (*Lindernia pyxidaria*), pickerel weed (*Monochloria vaginalis*), barnyardgrass (*Echinochloa crus-galli*), slender spikerush (*Eleocharia acicularis*) and hotarui (*Scirpus acutus*), etc.

Accordingly, the methylurea derivatives (I) are useful as the selective herbicides applicable to wheat, corn, cotton, soybean and rice plants. Further, they are useful as the herbicides to be applied for non-agricultural land because of their strong herbicidal potency.

As stated above, the methylurea derivatives (I) are novel and can be synthesized by various procedures, of which the typical examples are described below.

Procedure A:

The methylurea derivative (I) can be prepared by reacting a phenyl isocyanate compound of the formula:

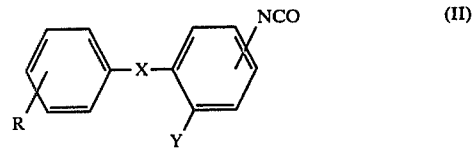

wherein R, X and Y are each as defined above and the isocyanato group is present at the m- or p-position to the group of the formula:

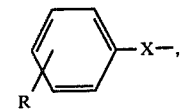

with dimethylamine or N,O-dimethylhydroxylamine.

The reaction may be carried out in water or an organic solvent (e.g. benzene, toluene, xylene, diethylether, tetrahydrofuran, dioxane, N,N-dimethylformamide, chloroform, carbon tetrachloride), or their mixture at a temperature of 0° to 50° C. instantaneously or within 10 hours.

Procedure B:

The methylurea derivative (I) (A: CH₃) can be prepared by methylating an N'-phenyl-N-hydroxyurea compound of the formula:

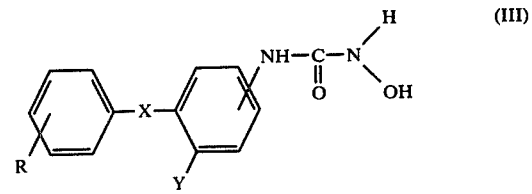

wherein R, X and Y are each as defined above and the substituted ureido group is present at the m- or p-position to the group:

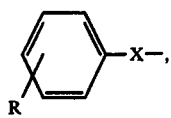

with a methylating agent (e.g. methyl iodide, dimethyl sulfate, diazomethane).

The reaction conditions may be appropriately chosen depending on the kind of the methylating agent. In case of using dimethyl sulfate as the methylating agent, for instance, the reaction may be carried out in water or an organic solvent (e.g. benzene, toluene, xylene, methanol, ethanol, isopropanol, diethyl ether, tetrahydrofuran, dioxane, methylene chloride), or their mixture in the presence of a base such as sodium hydroxide or potassium hydroxide. A phase transfer catalyst such as a quaternary ammonium salt may be also present in the reaction system to obtain the objective compound (I) in a good yield. The reaction is usually carried out at a temperature of 0° to 100° C. instantaneously or within 10 hours.

Procedure C:

The methylurea derivative (I) can be prepared by reacting an aniline compound of the formula:

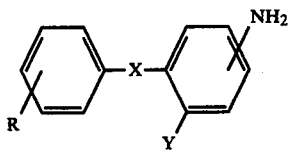

wherein R, X and Y are each as defined above and the amino group is present at the m- or p-position to the group:

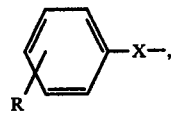

with N-methoxy-N-methylcarbamyl chloride or N,N-dimethylcarbamyl chloride.

The reaction may be carried out in an organic solvent (e.g. benzene, toluene, xylene, diethyl ether, tetrahydrofuran, dioxane, chloroform, carbon tetrachloride, ethyl acetate, pyridine, dimethylformamide) or its mixture at a temperature of 0° to 150° C. instantaneously or within 10 hours. A base such as pyridine, triethylamine, sodium hydroxide or potassium hydroxide may be advantageously used as an acid-eliminating agent to obtain the objective compound (I) in a good yield.

The phenyl isocyanate compound (II), which is the starting material in Procedure A, is obtainable by reacting the aniline compound (IV) with phosgene. The reaction is carried out in an organic solvent (e.g. benzene, toluene, xylene, tetrahydrofuran, dioxane, chloroform, carbon tetrachloride, ethyl acetate) at a temperature from room temperature (e.g. 20° C.) to the refluxing temperature of the reaction system instantaneously or within 10 hours.

The N'-phenyl-N-hydroxyurea compound (III) used as the starting material in Procedure B can be obtained by reacting the phenyl isocyanate compound (II) with hydroxylamine. This reaction is carried out in water or an organic solvent (e.g. benzene, toluene, xylene, diethylether, tetrahydrofuran, dioxane, chloroform, carbon tetrachloride), or their mixture at a temperature from 0° to 50° C. instantaneously or within 10 hours.

The aniline compound (IV), which is the common starting material in Procedures A to C, can be obtained by reduction of the corresponding nitrobenzene compound of the formula:

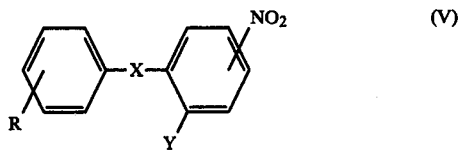

wherein R, X and Y are each as defined above and the nitro group is present at the m- or p-position to the group:

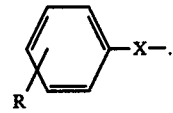

The reduction may be accomplished by any per se conventional procedure such as catalytic reduction using platinum oxide, Raney nickel, platinum black or palladium carbon, reduction using a metal (e.g. tin, iron, zinc) and an acid (e.g. hydrochloric acid, sulfuric acid), reduction using a metal (e.g. sodium, lithium, aluminum, magnesium, zinc) in an alcohol, reduction using sodium or zinc with an alkali hydroxide or an alkali alcoholate, reduction using an inorganic compound (e.g. stannus chloride, ferrous sulfate, ferrous hydroxide, sodium sulfide, sodium polysulfide, ammonium sulfide, hydrogen sulfide) or reduction with a hydrazine compound (e.g. hydrazine, phenylhydrazine), etc. For instance, in case of the catalytic reduction using palladium carbon, the reaction may be effected under hydrogen atmosphere in an organic solvent (e.g. benzene, toluene, methanol, ethanol, isopropanol, tetrahydrofuran, dioxane) or its mixture under atmospheric or elevated pressure for a period of 30 minutes to 10 hours.

The said nitrobenzene compound (V) is known when R is hydrogen and Y is hydrogen [Ann., 598, 167–173 (1956); J. Pharm. Sci., 56, (6), 737–742 (1967)]; in the case that R and Y have other meanings, it may be produced by any similar procedure to the one as disclosed in the said literatures. Particularly, the nitrogenzene compound (V) is obtainable by reacting the phenylalkyltriphenylphosphonium halide compound of the formula:

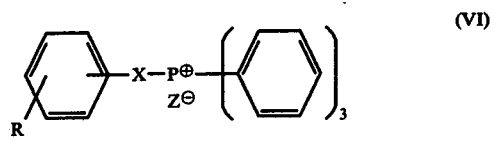

wherein R and X are each as defined above and Z is a halogen atom (e.g. chlorine, bromine) with the nitrobenzaldehyde compound of the formula:

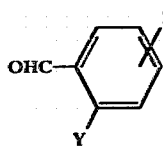

$$\text{(VII)}$$

wherein Y is as defined above. The reaction may be carried out in the presence of a base (e.g. n-butyl lithium, sodium hydride) in an inert organic solvent (e.g. ether, tetrahydrofuran, dimethylsulfoxide) at a temperature from $-10°$ to $100°$ C. for a period of 30 minutes to 10 hours.

Specific examples of the methylurea derivative (I) are shown below:

| Compound No. | Structure | Physical property |
|---|---|---|
| 1 | Ph—CH₂CH₂CH₂—C₆H₄—NH—C(=O)—N(CH₃)(CH₃) | M.P. 114–114.5° C. |
| 2 | Ph—CH₂CH₂CH₂—C₆H₄—NH—C(=O)—N(CH₃)(OCH₃) | $n_D^{22.0}$ 1.5471 |
| 3 | Ph—CH₂CH₂CH₂—C₆H₄—NH—C(=O)—N(CH₃)(CH₃) | M.P. 102.5–103° C. |
| 4 | Ph—CH₂CH₂CH₂—C₆H₄—NH—C(=O)—N(CH₃)(OCH₃) | $n_D^{22.0}$ 1.5640 |
| 5 | 3-CH₃-C₆H₄—CH₂CH₂CH₂—C₆H₄—NH—C(=O)—N(CH₃)(CH₃) | M.P. 80–81° C. |
| 6 | 3-CH₃-C₆H₄—CH₂CH₂CH₂—C₆H₄—NH—C(=O)—N(CH₃)(OCH₃) | $n_D^{21.0}$ 1.5870 |
| 7 | 3-CH₃-C₆H₄—CH₂CH₂CH₂—C₆H₄—NH—C(=O)—N(CH₃)(CH₃) | $n_D^{21.0}$ 1.5750 |
| 8 | 3-CH₃-C₆H₄—CH₂CH₂CH₂—C₆H₄—NH—C(=O)—N(CH₃)(OCH₃) | $n_D^{21.0}$ 1.5645 |
| 9 | 3-CH₃-C₆H₄—CH₂CH=CH—C₆H₄—NH—C(=O)—N(CH₃)(CH₃) | $n_D^{21.0}$ 1.6090 |

-continued

| Compound No. | Structure | Physical property |
|---|---|---|
| 10 | 3-CH₃-C₆H₄-CH₂CH=CH-C₆H₄-NH-C(=O)-N(CH₃)(OCH₃) | $n_D^{21.0}$ 1.6075 |
| 11 | 4-CH₃-C₆H₄-CH₂CH₂CH₂-C₆H₄-NH-C(=O)-N(CH₃)₂ | M.P. 92.5–93° C. |
| 12 | 4-CH₃-C₆H₄-CH₂CH₂CH₂-C₆H₄-NH-C(=O)-N(CH₃)(OCH₃) | $n_D^{22.0}$ 1.5690 |
| 13 | 4-CH₃-C₆H₄-CH₂CH₂CH₂-C₆H₄-NH-C(=O)-N(CH₃)₂ | M.P. 113–114° C. |
| 14 | 4-CH₃-C₆H₄-CH₂CH₂CH₂-C₆H₄-NH-C(=O)-N(CH₃)(OCH₃) | $n_D^{25.5}$ 1.5809 |
| 15 | C₆H₅-CH₂CH₂CH₂CH₂-C₆H₄-NH-C(=O)-N(CH₃)₂ | M.P. 84.5–85° C. |
| 16 | C₆H₅-CH₂CH₂CH₂CH₂-C₆H₄-NH-C(=O)-N(CH₃)(OCH₃) | $n_D^{20.5}$ 1.5662 |
| 17 | 4-CH₃-C₆H₄-CH₂CH₂CH₂CH₂-C₆H₄-NH-C(=O)-N(CH₃)₂ | M.P. 146.5–147° C. |
| 18 | 4-CH₃-C₆H₄-CH₂CH₂CH₂CH₂-C₆H₄-NH-C(=O)-N(CH₃)(OCH₃) | M.P. 78.5–79° C. |
| 19 | 2-C₂H₅-C₆H₄-CH₂CH=CH-(4-Cl-C₆H₃)-NH-C(=O)-N(CH₃)₂ | M.P. 86–88° C. |
| 20 | 2-C₂H₅-C₆H₄-CH₂CH=CH-(4-Cl-C₆H₃)-NH-C(=O)-N(CH₃)(OCH₃) | $n_D^{23}$ 1.5872 |

-continued

| Compound No. | Structure | Physical property |
|---|---|---|
| 21 | 2-CH₃-C₆H₄-CH₂CH₂CH₂-C₆H₄-NH-C(=O)-N(CH₃)₂ | M.P. 83–84° C. |
| 22 | 2-CH₃-C₆H₄-CH₂CH₂CH₂-C₆H₄-NH-C(=O)-N(CH₃)(OCH₃) | M.P. 93–94° C. |
| 23 | t-C₄H₉-C₆H₄-CH₂CH₂CH₂-C₆H₄-NH-C(=O)-N(CH₃)₂ | M.P. 103–104° C. |
| 24 | t-C₄H₉-C₆H₄-CH₂CH₂CH₂-C₆H₄-NH-C(=O)-N(CH₃)(OCH₃) | $n_D^{25}$ 1.5525 |

Some practical embodiments of the process for preparing the methylurea derivative (I) are illustratively shown below.

EXAMPLE 1

Synthesis of N'-3-(3-phenylpropyl)phenyl-N,N-dimethylurea according to Procedure A:

Through a solution of 3-(3-phenylpropyl)phenyl isocyanate (2.0 g) in 30 ml of benzene was bubbled an excessive amount of anhydrous dimethylamine in 10 minutes at a temperature below 30° C. After stirring for 30 minutes at room temperature, the solvent was removed under reduced pressure. The precipitated crystals were collected and washed with ether to give 2.1 g of N'-3-(3-phenylpropyl)-N,N-dimethylurea as white crystals (yield, 88%). M.P. 102.5°–103° C.

Elementary analysis: Calcd. for $C_{18}H_{22}N_2O$: C, 76.56%; H, 7.85%; N, 9.92%. Found: C, 76.54%; H, 7.84%; N, 9.94%.

EXAMPLE 2

Synthesis of N'-3-(3-phenylpropyl)phenyl-N-methoxy-N-methylurea according to Procedure B:

To a solution of N'-3-(3-phenylpropyl)phenyl-N-hydroxyurea (5.4 g) and dimethyl sulfate (5.5 g) in 60 ml of toluene was added 0.065 g of tetra-n-butylammonium bromide. Aqueous 10 N sodium hydroxide solution (4.4 ml) was dropwise added to the mixture at 20°–22° C. for 30 minutes with stirring, and stirring was continued at the same temperature for 3 hours. The organic layer was separated, washed with water and dried over anhydrous sodium sulfate. Removal of the solvent gave 5.7 g of N'-3-(3-phenylpropyl)phenyl-N-methoxy-N-methylurea as white crystals (yield, 95%). $n_D^{22.0}$ 1.5640.

Elementary analysis: Calcd. for $C_{18}H_{22}N_2O_2$: C, 72.45%; H, 7.43%; N, 9.39%. Found: C, 72.42%; H, 7.45%; N, 9.38%.

EXAMPLE 3

Synthesis of N'-3-[3-(3-methylphenyl)propyl]phenyl-N-methoxy-N-methylurea according to Procedure C:

To a solution of 3-[3-(3-methylphenyl)propyl]aniline (1.5 g) in 10 ml of pyridine was dropwise added a solution of N-methoxy-N-methylcarbamyl chloride (0.9 g) in 1 ml of benzene for 15 minutes under ice-cooling. After allowed to stand at room temperature for 12 hours, the resultant mixture was poured into ice-water, followed by extraction with ethyl acetate. The extract was washed with water and dried over magnesium sulfate. The solvent was removed under reduced pressure, and the oily residue was subjected to purification by silica gel chromatography using a mixture of benzene and tetrahydrofuran as an eluent to give 2.0 g of N'-3-[3-(3-methylphenyl)propyl]phenyl-N-methoxy-N-methylurea (yield, 96%). $n_D^{21.0}$ 1.5870.

Elementary analysis: Calcd. for $C_{19}H_{24}O_2N_2$: C, 73.04%; H, 7.74%; N, 8.97%. Found: C, 73.06%; H, 7.70%; N, 8.98%.

Some practical embodiments of the production of the starting materials are shown below.

EXAMPLE 4

Synthesis of 3-(3-phenyl-1-propenyl)aniline:

To a solution of 3-(3-phenyl-1-propenyl)nitrobenzene (10.5 g) in 200 ml of ethanol were added 70 ml of 35% ammonia water and 44 g of sodium disulfide. After heating under reflux for 2 hours, the solvent was removed under reduced pressure, followed by extraction with ethyl acetate. The extract was washed with water and dried over magnesium sulfate. The solvent was removed by distillation under reduced pressure to give 7.8 g of 3-(3-phenyl-1-propenyl)aniline (yield, 85%). B.P. 128°–130° C./0.09 mmHg.

Elementary analysis: Calcd. for $C_{15}H_{15}N$: C, 86.08%; H, 7.22%; N, 6.69%. Found: C, 86.11%; H, 7.21%; N, 6.67%.

EXAMPLE 5

Synthesis of 3-(3-phenylpropyl)aniline:

A solution of 3-(3-phenyl-1-propenyl)aniline (3.6 g) in 50 ml of ethanol was subjected to catalytic reduction using 1 g of 10% palladium-carbon. After removal of the catalyst by filtration, the solvent was removed under reduced pressure. The residue was distilled under reduced pressure to give 3.3 g of 3-(3-phenylpropyl)aniline (yield, 92%). B.P. 122°–126° C./0.08 mmHg.

Elementary analysis: Calcd. for $C_{15}H_{17}N$: C, 85.26%; H, 8.11%; N, 6.63%. Found: C, 85.27%; H, 8.09%; N, 6.64%.

EXAMPLE 6

Synthesis of 3-(3-phenylpropyl)phenyl isocyanate:

To a solution of 3-(3-phenylpropyl)aniline (11.6 g) in 100 ml of toluene was dropwise added a solution of phosgene (20 g) in 100 ml of toluene at 10°–20° C. The resultant mixture was gradually heated and, after refluxed for 30 minutes, allowed to cool to room temperature. The solvent was removed under reduced pressure, and the residue was distilled under reduced pressure to give 11.6 g of 3-(3-phenylpropyl)phenyl isocyanate (yield, 89%). B.P. 121°–125° C./0.2 mmHg.

Elementary analysis: Calcd. for $C_{16}H_{15}ON$: C, 80.98%; H, 6.37%; N, 5.90%. Found: C, 80.99%; H, 6.35%; N, 5.93%.

EXAMPLE 7

Synthesis of N'-3-(3-phenylpropyl)phenyl-N-hydroxyurea:

To a solution of hydroxylamine hydrochloride (6.7 g) in 10 ml of water was dropwise added 9.7 ml of aqueous 10 N sodium hydroxide solution under ice-cooling. To the mixture, a solution of 3-(3-phenylpropyl)phenyl isocyanate (4.0 g) in 50 ml of toluene was dropwise added at a temperature below 10° C. After allowed to stand at room temperature overnight, the resultant mixture was extracted with ethyl acetate. The ethyl acetate layer was washed with water and dried over magnesium sulfate. The solvent was removed under reduced pressure to give 4.5 g of N'-3-(3-phenylpropyl)phenyl-N-hydroxyurea (yield, 98%). M.P. 94°–96° C.

Elementary analysis: Cacld. for $C_{16}H_{18}O_2N_2$: C, 71.09%; H, 6.71%; N, 10.36%. Found: C, 71.07%; H, 6.73%; N, 10.33%.

EXAMPLE 8

Synthesis of 4-[3-(4-methylphenyl)propyl]aniline:

To a solution of 4-[3-(4-methylphenyl)-1-propenyl]nitrobenzene (20 g) in ethanol (100 ml), 10% palladium-carbon (10 g) was added, and the resultant mixture was subjected to catalytic reduction under a pressure of 50 atm. After removal of the solvent from the reaction mixture by distillation, the residue was distilled under reduced pressure to give 4-[3-(4-methylphenyl)propyl]aniline (16.2 g). B.P. 135°–145° C./0.15 mmHg.

Elementary analysis: Calcd. for $C_{16}H_{19}N$: C, 85.28%; H, 8.50%; N, 6.22%. Found: C, 85.31%; H, 8.24%; N, 6.13%.

EXAMPLE 9

Synthesis of 4-[3-(4-methylphenyl)-1-propenyl]nitrobenzene:

To a suspension of [2-(4-methylphenyl)ethyl]triphenyl-phosphonium bromide (55.4 g) in anhydrous tetrahydrofuran (840 ml) kept at $-50°$ C., a 1.5 N solution of n-butyl lithium in hexane (80 ml) was added, and the resultant mixture was stirred for a while. A solution of p-nitrobenzaldehyde (15.1 g) in anhydrous tetrahydrofuran (100 ml) was added thereto. The resulting mixture was allowed to stand at room temperature overnight, diluted with water and extracted with ethyl acetate. The extract was concentrated under reduced pressure and chromatographed on a column with silica gel, followed by eluting with a mixture of hexane and ethyl acetate to give 4-[3-(4-methylphenyl)-1-propenyl]nitrobenzene (21 g). $n_D^{24}$ 1.5321.

Elementary analysis: Calcd. for $C_{16}H_{15}NO_2$: C, 75.87%; H, 5.97%; N, 5.53%. Found: C, 75.91%; H, 5.82%; N, 5.46%.

In the practical usage of the methylurea derivatives (I), they may be applied as such or in any preparation form such as wettable powders, emulsifiable concentrates, granules, fine granules, dusts or suspensions.

For production of said preparation forms, solid or liquid carriers or diluents may be used. As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol, ethanol, ethylene glycol, benzyl alcohol), aromatic hydrocarbons (e.g. benzene, toluene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of non-ionic, anionic, cationic and amphoteric ones. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the methylurea derivatives (I) may be usually from 1 to 95% by weight, preferably from 1 to 80% by weight.

Practical embodiments of the herbicidal composition according to the invention are illustratively shown in the following examples wherein part(s) and % are by weight.

PREPARATION EXAMPLE 1

Eighty parts of Compound No. 4, 5 parts of polyoxyethylene alkylaryl ether and 15 parts of synthetic silica hydrate are well mixed while being powdered to obtain a wettable powder preparation.

PREPARATION EXAMPLE 2

Thirty parts of Compound No. 1, 7 parts of polyoxyethylene alkylaryl ether, 3 parts of alkylaryl sulfonate and 60 parts of xylene are well mixed to obtain an emulsifiable concentrate preparation.

PREPARATION EXAMPLE 3

One part of Compound No. 3, 1 part of white carbon, 5 parts of ligninsulfonate and 93 parts of clay are well mixed while being powdered. The mixture is then well kneaded with water, granulated and dried to obtain a granule preparation.

PREPARATION EXAMPLE 4

Fourty parts of bentonite, 5 parts of lignin-sulfonate and 55 parts of clay are well mixed while being powdered. The mixture is then well kneaded with water, granulated and dried to obtain a granule containing no active ingredient. The granule is then impregnated with 5 parts of Compound No. 4 to obtain a granule preparation.

PREPARATION EXAMPLE 5

Three parts of Compound No. 6, 0.5 part of isopropyl phosphate, 66.5 parts of clay and 30 parts of talc are well mixed while being powdered to obtain a dust preparation.

PREPARATION EXAMPLE 6

Twenty parts of Compound No. 15 is mixed with 60 parts of an aqueous solution containing 3% polyoxyethylene sorbitan monolactate and ground until the particle size of the active ingredient becomes less than 3 microns. Twenty parts of an aqueous solution containing 3% of sodium alginate as a dispersing agent is introduced therein to obtain a suspension preparation.

The methylurea derivatives (I) may be used together with other herbicides to improve their herbicidal activity, and in some cases, to produce a synergistic effect. As the other herbicides, there may be given phenoxy series herbicides such as 2,4-dichlorophenoxyacetic acid and 2,4-dichlorophenoxybutyric acid (including esters and salts thereof); diphenyl ether series heribicides such as 2,4-dichlorophenyl-4'-nitrophenyl ether, 2,4-dichlorophenyl-4'-nitro-3-methoxyphenyl ether, 2,4-dichlorophenyl-3-methoxycarbonyl-4-nitrophenyl ether and 2-chloro-4-trifluoromethylphenyl-3-hydroxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine and 2-methylthio-4,6-bisethylamino-1,3,5-triazine; urea series herbicides such as 3-(3,4-dichlorophenyl)-1,1-dimethylurea, 3-(3,4-dichlorophenyl)-1-methoxy-1-methylurea, 3-(4-isopropylphenyl)-1,1-dimethylurea, 3-[4-(4-chlorophenoxy)phenyl]-1,1-dimethylurea and 3-($\alpha,\alpha,\alpha$-trifluoro-m-tolyl)-1,1-dimethylurea; carbamate series herbicides such as isopropyl-N-(3-chlorophenyl)-carbamate, methyl-N-(3,4-dichlorophenyl)carbamate and 4-chloro-2-butynyl-m-chlorocarbanylate; thiolcarbamate series herbicides such as S-(4-chlorobenzyl)-N,N-diethylthiolcarbamate and S-ethyldipropylthiolcarbamate; acid anilide series herbicides such as 3,4-dichloropropionanilide, N-methoxymethyl-2,6-diethyl-2-chloroacetanilide and 2-chloro-2',6'-diethyl-N-butoxymethylacetanilide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; phosphorus series herbicides such as N-(phosphonomethyl)glycine, O-methyl-O-(2-nitro-4-methylphenyl)-N-isopropylphosphoroamidothioate and O-ethyl-O-(2-nitro-5-methylphenyl)-N-sec-butylphosphoroamidothioate; toluidine series herbicide such as $\alpha,\alpha,\alpha$-trifluoro-2,6-dinitro-N,N-dipropyl-p-toluidine; N-sec-butyl-4-tert-butyl-2,6-dinitroaniline; 3,5-dinitro-$N^4,N^4$-dipropylsulfenylamide; 5-tert-butyl-3-(2,4-dichloro-5-isopropoxyphenyl)-1,3,4-oxadiazolin-2-one; 3-isopropyl-1H-2,1,3-benzothiadiazin-4-(3H)-one-2,2-dioxide (including salt thereof); 2-($\beta$-naphthoxy)propionanilide; 2-($\alpha$-naphthoxy)-N,N-diethylpropionamide; 3-amino-2,5-dichlorobenzoate; 2-sec-butyl-4,6-dinitrophenyl; N-1-naphthylphthalamine and the like. But, the herbicides are not limited to these examples.

The herbicides of the invention may be applied together with microbicidal agricultural chemicals, organic phosphorus series insecticides, carbamate series insecticides, pyrethroid series insecticides, other insecticides, fungicides, plant growth regulators, fertilizers, etc.

The dosage of the methylurea derivatives (I) depends upon their kinds, the preparation modes, the sorts of cultivated plants or weeds, weather, etc. Generally, however, the dosage of from 1 to 50 grams of the active ingredient per are is sufficient to control weeds as a selective herbicide. Within the dosage of from 10 to 200 grams of the active ingredient per are, a prominent nonselective herbicidal effect can be manifested.

The application of the methylurea derivatives (I) as herbicides will be illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively.

| Rating value | Fresh weight (percentage to untreated plot) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

Control (a)

-continued

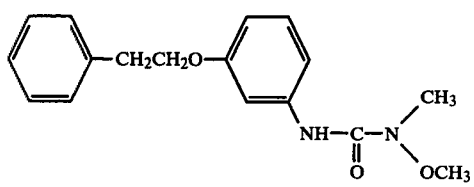
Belgian patent 871,562

Control (b)

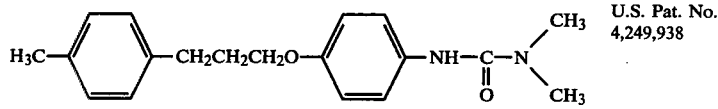
U.S. Pat. No. 4,249,938

Control (c)

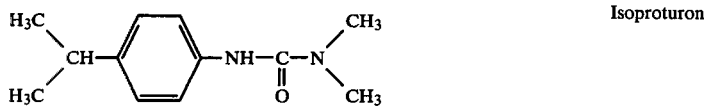
Isoproturon

Control (d)

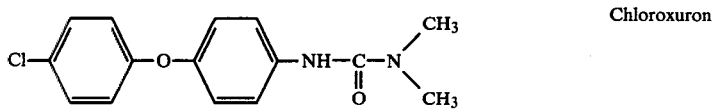
Chloroxuron

Control (e)

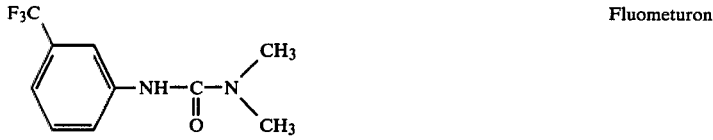
Fluometuron

EXAMPLE I

Post-emergence foliar treatment:

Plastic trays (35 cm × 25 cm × 10 cm) were filled with upland field soil, and the seeds of common lambs-quarters, wild mustard, wild buckwheat, common chickweed, red deadnettle, violet, quack grass, barnyard grass and green foxtail and the seeds of wheat were separately sowed in the trays and grown outdoors at the average temperature of 15° to 20° C. for 4 weeks. The designed amount of the test compound each formulated into an emulsifiable concentrate was sprayed to the foliage of the test plants over the top by means of a small hand sprayer. After the spraying, the test plants were grown outdoors for further 3 weeks, and the herbicidal activity and phytotoxicity were examined. The results are shown in Table 1. In this treatment, the emulsifiable concentrate was dispersed in water containing a wetting agent for application at a spray volume of 5 liters per are. The growing stage of the test plants on the application varied on their kind. However, the weeds were generally at 2 to 5 leaved stage and in 2 to 10 cm heights, and the wheat was at 4 leaved stage.

TABLE 1

| Compound No. | Dosage of active ingredient (g/are) | Phytotoxicity Wheat | Common lambs-quarters | Wild mustard | Wild buckwheat | Common chickweed | Red deadnettle | Violet | Quack grass | Barnyard grass | Green foxtail |
|---|---|---|---|---|---|---|---|---|---|---|---|
| 1 | 20 | 0 | 5 | 5 | 5 | 5 | 5 | 5 | 3 | 3 | 4 |
|   | 10 | 0 | 5 | 5 | 5 | 4 | 5 | 5 | 2 | 1 | 3 |
| 2 | 20 | 1 | 5 | 5 | 5 | 4 | 5 | 5 | 2 | 3 | 3 |
|   | 10 | 0 | 5 | 5 | 5 | 4 | 4 | 4 | 1 | 2 | 2 |
| 3 | 20 | 1 | 5 | 5 | 5 | 5 | 5 | 5 | 5 | 5 | 5 |
|   | 10 | 0 | 5 | 5 | 5 | 5 | 5 | 5 | 4 | 3 | 4 |
|   | 5 | 0 | 5 | 5 | 5 | 5 | 5 | 5 | 3 | 2 | 4 |
| 4 | 20 | 1 | 5 | 5 | 5 | 5 | 5 | 5 | 5 | 5 | 5 |
|   | 10 | 0 | 5 | 5 | 5 | 5 | 5 | 5 | 5 | 4 | 5 |
|   | 5 | 0 | 5 | 5 | 5 | 5 | 5 | 5 | 4 | 4 | 4 |
| 5 | 20 | 0 | 5 | 5 | 5 | 5 | 5 | 5 | 4 | 4 | 5 |
|   | 10 | 0 | 5 | 5 | 5 | 4 | 5 | 5 | 2 | 3 | 3 |
| 6 | 20 | 0 | 5 | 5 | 5 | 5 | 5 | 5 | 5 | 4 | 4 |
|   | 10 | 0 | 5 | 5 | 5 | 5 | 5 | 5 | 3 | 3 | 4 |
| 7 | 20 | 0 | 5 | 5 | 5 | 4 | 5 | 5 | 4 | 3 | 4 |
|   | 10 | 0 | 5 | 5 | 5 | 4 | 4 | 5 | 2 | 2 | 3 |
| 9 | 20 | 0 | 5 | 5 | 5 | 5 | 5 | 5 | 3 | 3 | 4 |
|   | 10 | 0 | 5 | 5 | 5 | 4 | 5 | 5 | 1 | 2 | 2 |
| 11 | 20 | 0 | 5 | 5 | 5 | 5 | 5 | 5 | 4 | 4 | 4 |
|   | 10 | 0 | 5 | 5 | 5 | 5 | 5 | 5 | 2 | 3 | 3 |

TABLE 1-continued

| Compound No. | Dosage of active ingredient (g/are) | Phytotoxicity Wheat | Common lambsquarters | Wild mustard | Wild buckwheat | Common chickweed | Red deadnettle | Violet | Quack grass | Barnyard grass | Green foxtail |
|---|---|---|---|---|---|---|---|---|---|---|---|
| 12 | 20 | 1 | 5 | 5 | 5 | 5 | 5 | 5 | 5 | 4 | 4 |
|  | 10 | 0 | 5 | 5 | 5 | 5 | 5 | 5 | 3 | 3 | 3 |
| 13 | 20 | 0 | 5 | 5 | 5 | 5 | 5 | 5 | 4 | 3 | 4 |
|  | 10 | 0 | 5 | 5 | 5 | 5 | 5 | 5 | 2 | 2 | 3 |
| 14 | 20 | 0 | 5 | 5 | 5 | 5 | 5 | 5 | 4 | 3 | 4 |
|  | 10 | 0 | 5 | 5 | 5 | 4 | 5 | 5 | 2 | 1 | 2 |
| 15 | 20 | 0 | 5 | 5 | 5 | 5 | 5 | 5 | 3 | 4 | 4 |
|  | 10 | 0 | 5 | 5 | 5 | 5 | 5 | 5 | 2 | 3 | 3 |
| 16 | 20 | 1 | 5 | 5 | 5 | 5 | 5 | 5 | 4 | 4 | 4 |
|  | 10 | 1 | 5 | 5 | 5 | 5 | 5 | 5 | 3 | 3 | 2 |
| 17 | 20 | 0 | 5 | 5 | 5 | 5 | 5 | 5 | 4 | 3 | 4 |
|  | 10 | 0 | 5 | 5 | 5 | 4 | 5 | 4 | 3 | 2 | 4 |
|  | 5 | 0 | 5 | 4 | 5 | 3 | 4 | 3 | 2 | 1 | 2 |
| 18 | 40 | 0 | 5 | 5 | 5 | 5 | 5 | 5 | 3 | 4 | 4 |
|  | 20 | 0 | 5 | 5 | 5 | 4 | 5 | 4 | 3 | 3 | 3 |
| 20 | 20 | 0 | 5 | 5 | 5 | 5 | 5 | 5 | 4 | 4 | 5 |
|  | 10 | 0 | 5 | 5 | 5 | 5 | 5 | 5 | 3 | 3 | 3 |
| 21 | 20 | 0 | 5 | 5 | 5 | 5 | 5 | 5 | 5 | 4 | 4 |
|  | 10 | 0 | 5 | 5 | 5 | 5 | 5 | 5 | 3 | 3 | 3 |
| 22 | 20 | 1 | 5 | 5 | 5 | 5 | 5 | 5 | 4 | 5 | 5 |
|  | 10 | 1 | 5 | 5 | 5 | 5 | 5 | 5 | 3 | 3 | 4 |
| 23 | 20 | 1 | 5 | 5 | 5 | 5 | 5 | 5 | 4 | 4 | 4 |
|  | 10 | 0 | 5 | 5 | 5 | 5 | 5 | 5 | 3 | 3 | 2 |
| 24 | 20 | 1 | 5 | 5 | 5 | 5 | 5 | 5 | 5 | 5 | 5 |
|  | 10 | 1 | 5 | 5 | 5 | 5 | 5 | 5 | 4 | 3 | 5 |
| Control (a) | 20 | 4 | 5 | 5 | 5 | 4 | 5 | 5 | 4 | 4 | 5 |
|  | 10 | 2 | 5 | 5 | 5 | 4 | 4 | 4 | 3 | 3 | 4 |
|  | 5 | 2 | 5 | 4 | 5 | 3 | 3 | 2 | 2 | 1 | 2 |
| Control (b) | 20 | 2 | 5 | 5 | 5 | 4 | 4 | 4 | 3 | 2 | 4 |
|  | 10 | 1 | 5 | 4 | 5 | 3 | 2 | 3 | 2 | 1 | 3 |
|  | 5 | 0 | 5 | 4 | 4 | 2 | 1 | 2 | 1 | 0 | 1 |
| Control (c) | 20 | 1 | 5 | 4 | 3 | 5 | 2 | 3 | 3 | 2 | 4 |
|  | 10 | 0 | 5 | 2 | 2 | 4 | 2 | 2 | 2 | 1 | 4 |

EXAMPLE II

Post-emergence foliar treatment:

Plastic trays (35 cm × 25 cm × 10 cm) were filled with upland field soil, and the seeds of redroot pigweed, common lambsquarters, cocklebur, Jimson weed, black nightshade, sunflower, annual morningglory, velvetleaf and green foxtail and the seeds of corn, soybean and cotton were separately sowed in the trays and grown for 2 to 3 weeks in a greenhouse. The designed amount of the test compound each formulated into an emulsifiable concentrate was sprayed to the foliage of the test plants over the top by means of a small hand sprayer.

After the spraying, the test plants were grown for further 3 weeks in the greenhouse, and the herbicidal activity and phytotoxicity were examined. The results are shown in Table 2. In this treatment, the emulsifiable concentrate was dispersed in water containing a wetting agent for application at a spray volume of 5 liters per are.

The growing stage of the test plants varied on the application on their kind. However, the weeds were generally at 2 to 4 leaved stage and in 2 to 10 cm heights, and the corn was at 3 leaved stage, the soybean was at first compound stage and the cotton was at 1 leaved stage.

TABLE 2

| Compound No. | Dosage of active ingredient (g/are) | Phytotoxicity Corn | Soybean | Cotton | Redroot pigweed | Common lambsquarters | Cocklebur | Jimson weed | Black nightshade | Sunflower | Annual morningglory | Velvetleaf | Green foxtail |
|---|---|---|---|---|---|---|---|---|---|---|---|---|---|
| 1 | 20 | 1 | — | 1 | 5 | 5 | 5 | 5 | 5 | 5 | 5 | 5 | 4 |
|  | 10 | 0 | 1 | 1 | 5 | 5 | 5 | 5 | 5 | 4 | 5 | 5 | 3 |
| 3 | 20 | 1 | — | — | 5 | 5 | 5 | 5 | 5 | 5 | 5 | 5 | 5 |
|  | 10 | 1 | — | — | 5 | 5 | 5 | 5 | 5 | 5 | 5 | 5 | 4 |
|  | 5 | 0 | — | 1 | 5 | 5 | 5 | 5 | 5 | 5 | 5 | 5 | 3 |
| 4 | 20 | — | — | — | 5 | 5 | 5 | 5 | 5 | 5 | 5 | 5 | 5 |
|  | 10 | 1 | — | — | 5 | 5 | 5 | 5 | 5 | 5 | 5 | 5 | 5 |
|  | 5 | 0 | — | — | 5 | 5 | 5 | 5 | 5 | 5 | 5 | 5 | 4 |
| 5 | 20 | — | — | — | 5 | 5 | 5 | 5 | 5 | 5 | 5 | 5 | 5 |
|  | 10 | 1 | — | — | 5 | 5 | 5 | 5 | 5 | 5 | 5 | 5 | 3 |
| 6 | 20 | — | — | — | 5 | 5 | 5 | 5 | 5 | 5 | 5 | 5 | 5 |
|  | 10 | — | 1 | — | 5 | 5 | 5 | 5 | 5 | 5 | 5 | 5 | 4 |
| 7 | 20 | — | — | — | 5 | 5 | 5 | 5 | 5 | 5 | 5 | 5 | 4 |
|  | 10 | — | 1 | — | 5 | 5 | 5 | 5 | 5 | 5 | 5 | 5 | 2 |
| 8 | 40 | — | 1 | — | 5 | 5 | 5 | 5 | 5 | 5 | 5 | 5 | 3 |
|  | 20 | — | 0 | — | 5 | 5 | 4 | 5 | 4 | 5 | 4 | 5 | 2 |
| 12 | 20 | 1 | — | — | 5 | 5 | 5 | 5 | 5 | 5 | 5 | 5 | 4 |
|  | 10 | 0 | 1 | — | 5 | 5 | 5 | 5 | 5 | 5 | 5 | 5 | 3 |
| 13 | 20 | — | 0 | — | 5 | 5 | 5 | 5 | 5 | 5 | 5 | 5 | 4 |

TABLE 2-continued

| Compound No. | Dosage of active ingredient (g/are) | Phytotoxicity Corn | Phytotoxicity Soybean | Phytotoxicity Cotton | Herbicidal activity Redroot pigweed | Common lambsquarters | Cocklebur | Jimson weed | Black nightshade | Sunflower | Annual morningglory | Velvetleaf | Green foxtail |
|---|---|---|---|---|---|---|---|---|---|---|---|---|---|
|  | 10 | — | 0 | — | 5 | 5 | 4 | 5 | 5 | 5 | 4 | 5 | 2 |
| 14 | 40 | — | 0 | — | 5 | 5 | 5 | 5 | 5 | 5 | 5 | 5 | 4 |
|  | 20 | — | 0 | — | 5 | 5 | 5 | 5 | 5 | 5 | 4 | 5 | 3 |
| 16 | 20 | 1 | — | — | 5 | 5 | 5 | 5 | 5 | 5 | 5 | 5 | 4 |
|  | 10 | 1 | — | — | 5 | 5 | 5 | 5 | 5 | 5 | 5 | 5 | 3 |
| 17 | 20 | — | 1 | 1 | 5 | 5 | 5 | 5 | 5 | 5 | 5 | 5 | 4 |
|  | 10 | — | 1 | 0 | 5 | 5 | 5 | 5 | 5 | 5 | 4 | 5 | 3 |
| 24 | 20 | — | — | 1 | 5 | 5 | 5 | 5 | 5 | 5 | 5 | 5 | 5 |
|  | 10 | — | 1 | 0 | 5 | 5 | 5 | 5 | 5 | 5 | 5 | 5 | 5 |
| Control (d) | 20 | — | 3 | — | 5 | 5 | 5 | 5 | 5 | 5 | 5 | 4 | 3 |
|  | 10 | — | 2 | — | 5 | 5 | 5 | 5 | 5 | 3 | 4 | 2 | 2 |
| Control (e) | 20 | — | — | 1 | 5 | 5 | 5 | 5 | 5 | 5 | 5 | 5 | 4 |
|  | 10 | — | — | 1 | 5 | 5 | 3 | 5 | 5 | 4 | 4 | 3 | 3 |

EXAMPLE III (1) Pre-emergence treatment:

Plastic pots (each 500 ml volume) were filled with upland field soil, and the seeds of barnyard grass, wild oat (*Avena fatua*), annual morningglory and redroot pigweed were separately sowed in the pots. The designed amount of the test compound each formulated into an emulsifiable concentrate was sprayed to the soil surface by means of a small hand sprayer, and the thus treated soil was well mixed to the depth of 4 cm. After the spraying, the test plants were grown for further 3 weeks in a greenhouse, and the herbicidal activity was examined. The results are shown in Table 3. In this treatment, the emulsifiable concentrate was dispersed in water for application at a spray volume of 10 liters per are.

(2) Paddy field treatment:

Plastic pots (each 500 ml volume) were filled with paddy field soil containing the seeds of various weeds and, water was poured therein until the depth of water became 4 cm. Rice seedlings of 3 leaved stage and buds of slender spikerush, which tided over the winter, were planted into the pots and grown for 4 days in a greenhouse. The designed amount of the test compound each formulated into an emulsifiable concentrate was applied to the pots by perfusion. Three weeks after the application, the herbicidal activity and phytotoxicity were checked on the plants as well as the weeds such as barnyard grass, broad-leaved weeds (e.g. pickerel weed, false pimpernel, toothcup) and hotarui which were originally present in the paddy field soil. The results are shown in Table 3. In this treatment, the emulsifiable concentrate was dispersed in water for application at a perfusion volume of 10 liters per are.

TABLE 3

| Compound No. | Dosage of active ingredient (g/are) | Pre-emergence treatment Herbicidal activity | | | | Paddy field treatment | | | | Phytotoxicity |
|---|---|---|---|---|---|---|---|---|---|---|
|  |  | Barnyardgrass | Wild oat | Annual morningglory | Redroot pigweed | Barnyard grass | Broad-leaved grass | Slender spikerush | Hotarui | Rice plant |
| 2 | 40 | — | — | — | — | 3 | 5 | 5 | 5 | 1 |
| 3 | 40 | — | — | — | — | 2 | 5 | 5 | 2 | 1 |
| 4 | 40 | 1 | 1 | 5 | 5 | 5 | 5 | 5 | 5 | — |
|  | 10 | — | — | — | — | 4 | 5 | 5 | 4 | 0 |
| 5 | 40 | — | — | — | — | 4 | 5 | 4 | 3 | 0 |
| 6 | 40 | — | — | — | — | 5 | 5 | 4 | 4 | 0 |
| 7 | 40 | — | — | — | — | 3 | 5 | 4 | 2 | 0 |
| 9 | 40 | — | — | — | — | 4 | 5 | 4 | 3 | 0 |
| 10 | 40 | — | — | — | — | 4 | 5 | 4 | 4 | 0 |
| 11 | 40 | — | — | — | — | 4 | 5 | 5 | 4 | 1 |
|  | 10 | — | — | — | — | 3 | 5 | 4 | 2 | 0 |
| 12 | 40 | — | — | — | — | 4 | 5 | 4 | 5 | 0 |
| 14 | 40 | — | — | — | — | 4 | 5 | 3 | 3 | 1 |
| 16 | 40 | — | — | — | — | 4 | 5 | 5 | 4 | — |
|  | 10 | — | — | — | — | 2 | 5 | 4 | 2 | 0 |
| 18 | 40 | — | — | — | — | 4 | 5 | 4 | 4 | 0 |
| 19 | 40 | — | — | — | — | 3 | 5 | 5 | 3 | 0 |
| 20 | 40 | — | — | — | — | 3 | 5 | 5 | 4 | 0 |
| 21 | 40 | — | — | — | — | 4 | 5 | 5 | 4 | 1 |
| 24 | 40 | — | — | — | — | 4 | 5 | 5 | 5 | 1 |

What is claimed is:

1. A compound of the formula:

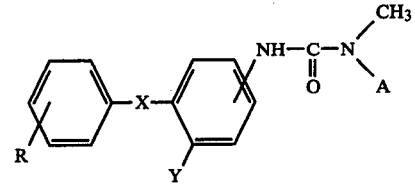

wherein R is a hydrogen atom or a $C_1$–$C_4$ alkyl group, X is a $C_3$–$C_4$ alkylene group or a $C_3$ alkenylene group, Y is a hydrogen atom or a chlorine atom, A is a methyl group or a methoxy group and the substituted ureido group is present at the m- or p-position to the group of the formula:

2. The compound according to claim 1, wherein X is a C$_3$–C$_4$ alkylene group, Y is a hydrogen atom and the substituted ureido group is present at the m- or p-position to the group of the formula:

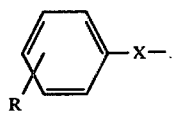

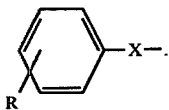

3. N'-3-(3-Phenylpropyl)phenyl-N-methoxy-N-methylurea.

4. N'-3-(3-Phenylpropyl)phenyl-N,N-dimethylurea.

5. N'-3-[3-(4-t-Butylphenyl)propyl]phenyl-N-methoxy-N-methylurea.

6. A herbicidal composition which comprises as an active ingredient a herbicidally effective amount of at least one of the compounds according to claim 1, and an inert carrier.

7. A method for controlling or exterminating weeds which comprises applying a herbicidally effective amount of at least one of the compounds according to claim 1 to the area where the weeds grow or will grow.

8. The method according to claim 7, wherein the area is a field of wheat.

* * * * *